(12) United States Patent
Csenar et al.

(10) Patent No.: US 11,752,267 B2
(45) Date of Patent: Sep. 12, 2023

(54) INJECTION DEVICE, IN PARTICULAR AUTOINJECTOR, FOR THE SIMULTANEOUS ADMINISTRATION OF SEVERAL MEDICATIONS

(71) Applicant: PHARMA CONSULT GES.M.B.H., Vienna (AT)

(72) Inventors: Markus Csenar, Vienna (AT); Andreas Schwirtz, Vienna (AT)

(73) Assignee: PHARMA CONSULT GES.M.B.H., Vienna (AT)

( * ) Notice: Subject to any disclaimer, the term of this patent is extended or adjusted under 35 U.S.C. 154(b) by 0 days.

(21) Appl. No.: 17/510,888

(22) Filed: Oct. 26, 2021

(65) Prior Publication Data
US 2022/0040409 A1 Feb. 10, 2022

Related U.S. Application Data

(63) Continuation of application No. 16/345,823, filed as application No. PCT/EP2017/077651 on Oct. 27, 2017, now abandoned.
(Continued)

(51) Int. Cl.
*A61M 5/20* (2006.01)
*A61M 5/24* (2006.01)
(Continued)

(52) U.S. Cl.
CPC ............ *A61M 5/2066* (2013.01); *A61M 5/20* (2013.01); *A61M 5/24* (2013.01); *A61M 5/2448* (2013.01);
(Continued)

(58) Field of Classification Search
CPC ........ A61M 5/2066; A61M 5/20; A61M 5/24; A61M 5/2448; A61M 5/326; A61M 5/19;
(Continued)

(56) References Cited

U.S. PATENT DOCUMENTS 3,572,336 A 3/1971 Hershberg
4,832,682 A * 5/1989 Sarnoff .......... C12Y 115/01001
604/137
(Continued)

FOREIGN PATENT DOCUMENTS

CN 1878587 A 12/2006
CN 101674857 A 3/2010
(Continued)

OTHER PUBLICATIONS

Office Action dated Nov. 22, 2022 in CN Appl. No. 202110967970.9.
(Continued)

*Primary Examiner* — Theodore J Stigell
(74) *Attorney, Agent, or Firm* — MEDLER FERRO WOODHOUSE & MILLS PLLC

(57) ABSTRACT

An injection device is disclosed for the administration of several medications. The injection device includes a carrying housing, an activation sleeve surrounding the carrying housing, at least two carpules, a first drive module for the administration of the medications, a securing device, a needle arrangement, a needle protection element, and a second triggerable drive module for the needle arrangement. The first drive module includes a drive element with a number of piston rods equal to the number of carpules. At least one of the piston rods is configured in the form of a hollow cylinder the is closed on the piston side, wherein arranged inside this is a first drive means of the first drive module. The first drive means can be arranged in an accommodation part of the drive element, wherein the accommodation part forms with the piston rods a composite structural unit.

18 Claims, 6 Drawing Sheets

Related U.S. Application Data

Figure 1:
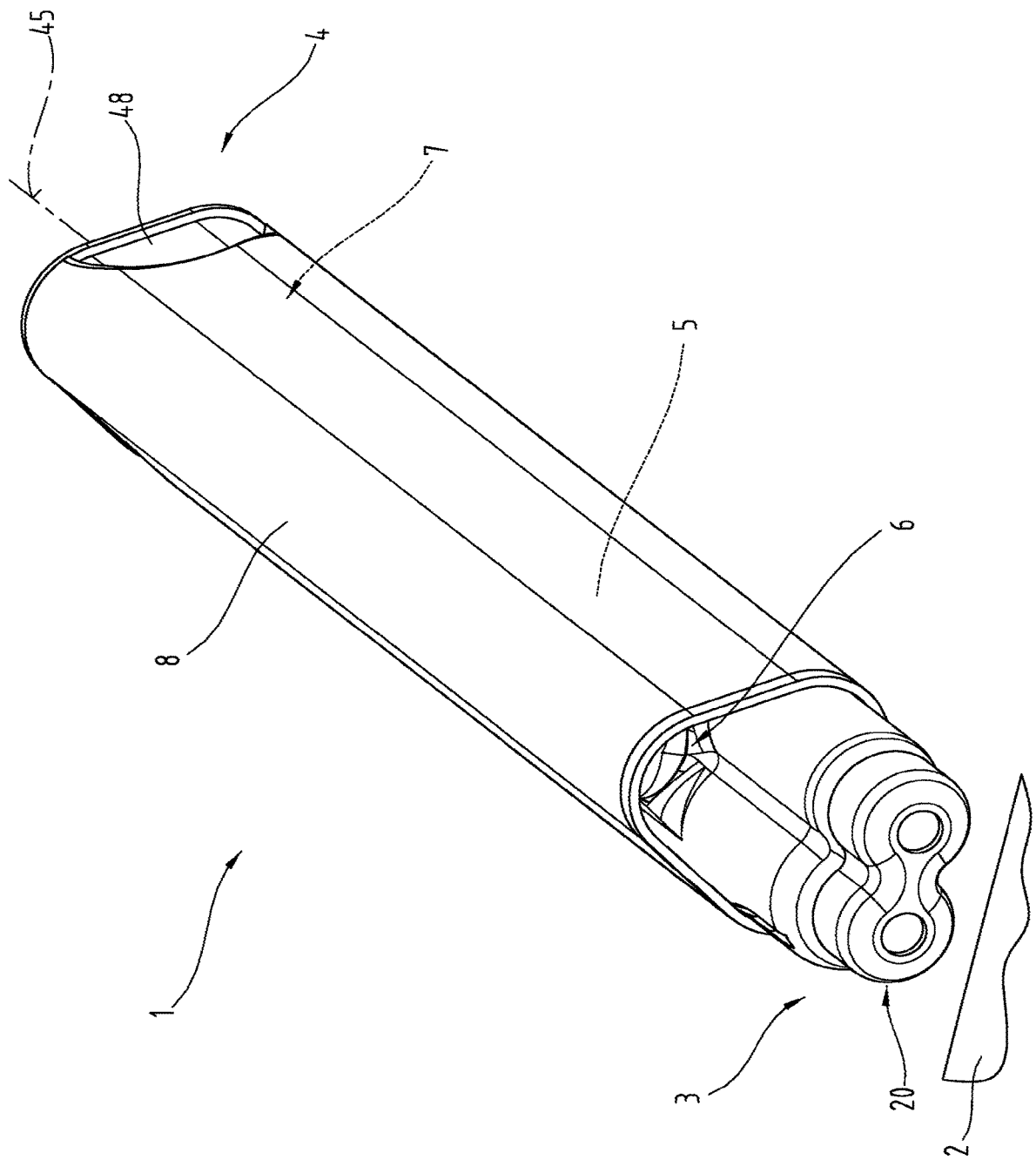

(60) Provisional application No. 62/413,557, filed on Oct. 27, 2016.

(51) Int. Cl.
*A61M 5/32* (2006.01)
*A61M 5/19* (2006.01)
*A61M 5/315* (2006.01)

(52) U.S. Cl.
CPC ............... *A61M 5/326* (2013.01); *A61M 5/19* (2013.01); *A61M 5/2033* (2013.01); *A61M 5/31596* (2013.01); *A61M 2005/206* (2013.01); *A61M 2005/2407* (2013.01)

(58) Field of Classification Search
CPC ............ A61M 5/2033; A61M 5/31596; A61M 2005/206; A61M 2005/2407
See application file for complete search history.

(56) References Cited

U.S. PATENT DOCUMENTS

| | | | |
|---|---|---|---|
| 10,252,005 B2 | 4/2019 | Bischoff et al. | |
| 2006/0264830 A1 | 11/2006 | Hommann | |
| 2008/0077084 A1 | 3/2008 | Hommann | |
| 2010/0152659 A1 | 6/2010 | Bollenbach et al. | |
| 2011/0125100 A1 | 5/2011 | Schwirtz et al. | |
| 2013/0312195 A1 | 11/2013 | Berube | |
| 2013/0317477 A1 | 11/2013 | Edwards et al. | |
| 2016/0144117 A1 | 5/2016 | Chun | |

FOREIGN PATENT DOCUMENTS

| | | |
|---|---|---|
| CN | 105722539 A | 6/2016 |
| EP | 0014006 A2 | 8/1980 |
| EP | 0055039 B1 | 5/1985 |
| EP | 0191771 B1 | 7/1994 |
| EP | 2438941 A1 | 4/2012 |
| FR | 447368 A | 12/1912 |
| FR | 1514210 A | 2/1968 |
| JP | H0613051 B2 | 2/1994 |
| JP | 2008-529686 A | 8/2008 |
| JP | 2011-524212 A | 9/2011 |
| JP | 2012-200360 A | 10/2012 |
| WO | 85/02775 A1 | 7/1985 |
| WO | 86/01120 A1 | 2/1986 |
| WO | 86/06967 A1 | 12/1986 |
| WO | 94/03392 A1 | 2/1994 |
| WO | 94/11039 A1 | 5/1994 |
| WO | 2009/152542 A1 | 12/2009 |
| WO | 2014/060563 A2 | 4/2014 |
| WO | 2014/205604 A1 | 12/2014 |
| WO | 2015/118140 A1 | 8/2015 |
| WO | 2015/181191 A1 | 12/2015 |
| WO | 2015/181192 A1 | 12/2015 |

OTHER PUBLICATIONS

Search Report dated Nov. 14, 2022 in CN Appl. No. 202110967970.9.
Japanese Office Action dated Jun. 29, 2021 in JP Patent Application No. 2019-522397, corresponding to parent U.S. Appl. No. 16/345,823.
Chinese Office Action dated Feb. 8, 2021 in CN Patent Application No. 201780066659.9, corresponding to parent U.S. Appl. No. 16/345,823.
International Search Report dated Feb. 13, 2018 for Appl. No. PCT/EP2017/077651, 5 pages.
Written Opinion of the International Searching Authority dated Feb. 13, 2018 for Appl. No. PCT/EP2017/077651, 6 pages.

* cited by examiner

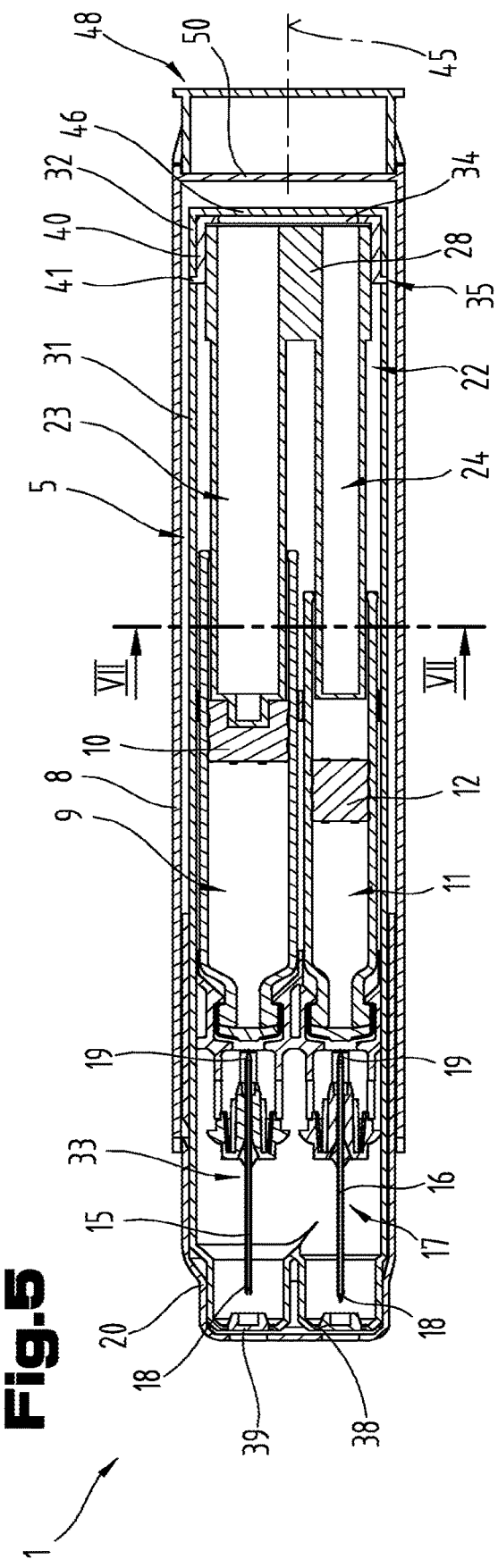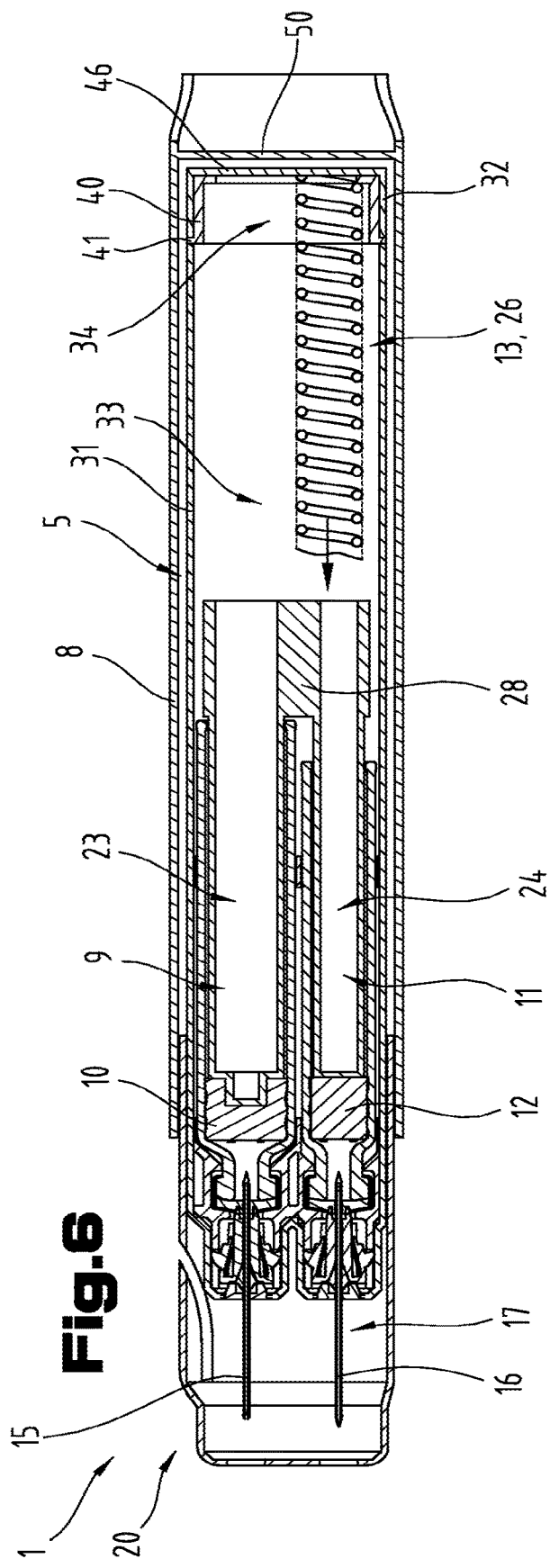

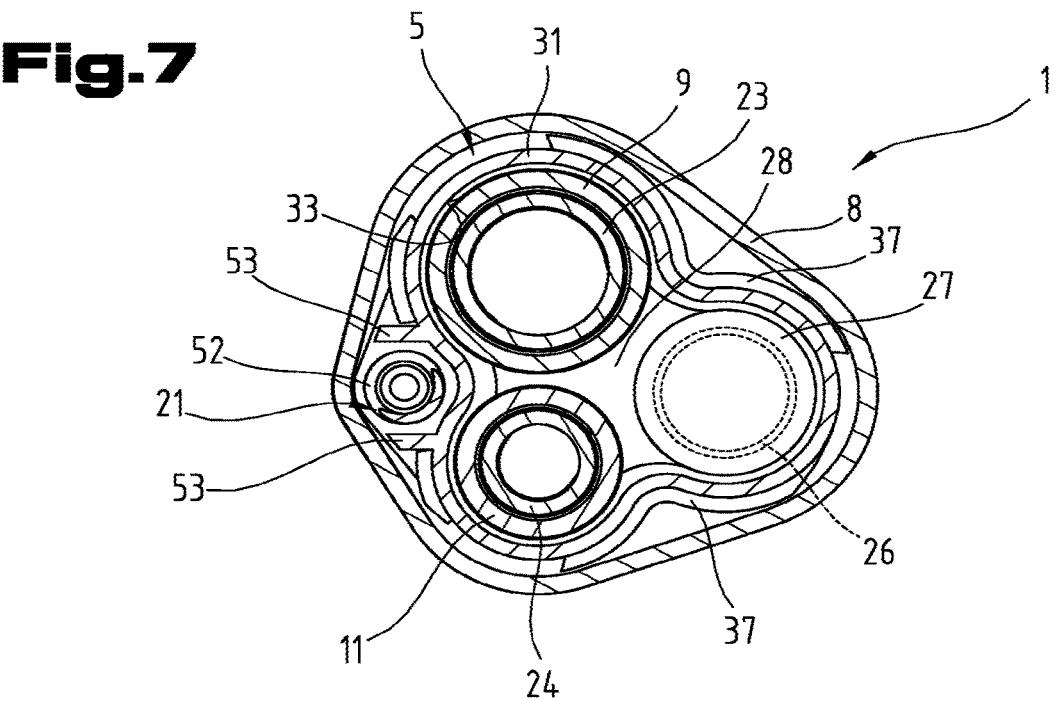
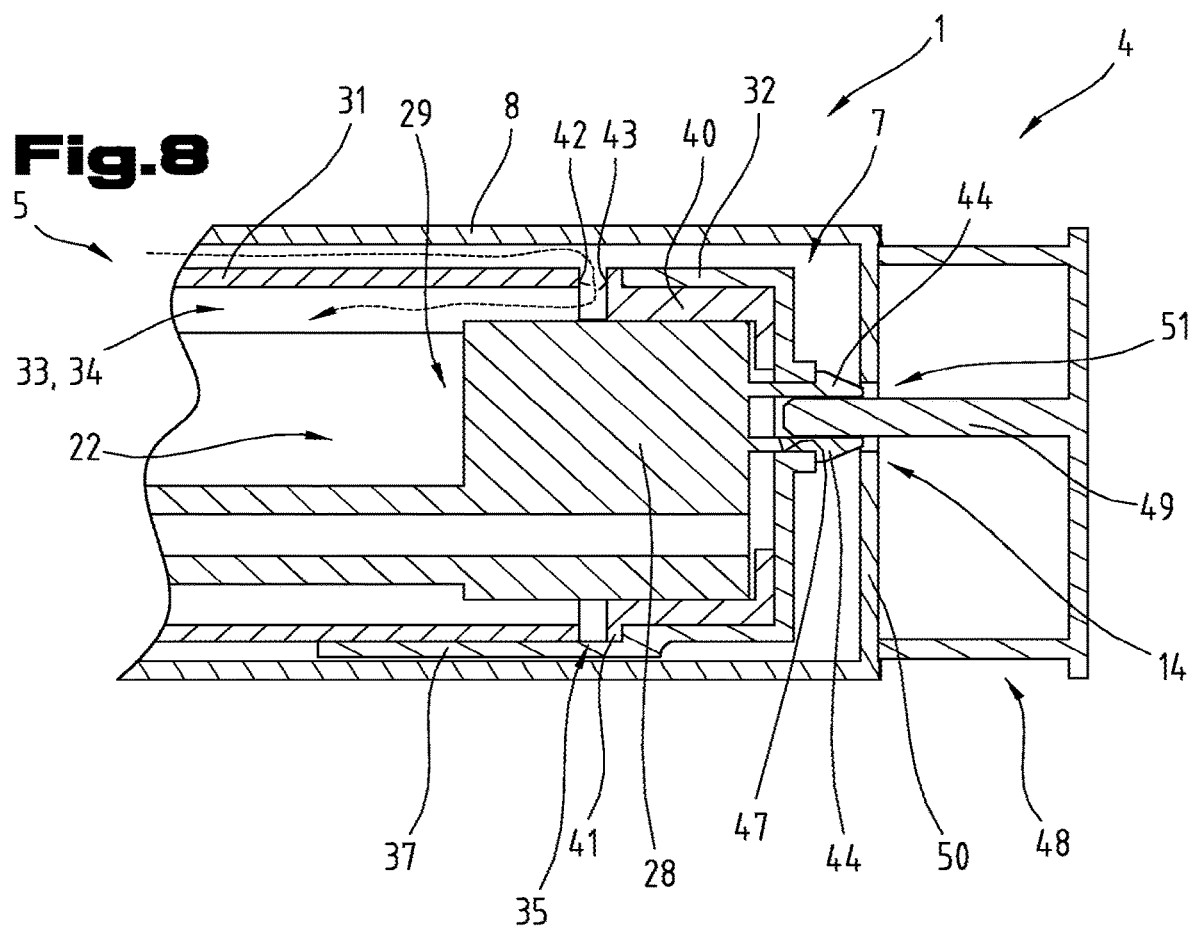

INJECTION DEVICE, IN PARTICULAR AUTOINJECTOR, FOR THE SIMULTANEOUS ADMINISTRATION OF SEVERAL MEDICATIONS

CROSS-REFERENCE TO RELATED APPLICATION(S)

The present application is a continuation of prior U.S. application Ser. No. 16/345,823, filed Apr. 29, 2019, which is a National Stage Entry of International Application No. PCT/EP2017/077651, filed Oct. 27, 2017, which claims the benefit of prior U.S. Application No. 62/413,557, filed Oct. 27, 2016, the entire contents of which are incorporated by reference herein.

FIELD OF THE INVENTION

The invention relates to an injection device, in particular an autoinjector, for the simultaneous administration of at least two medications.

BACKGROUND OF THE INVENTION

From WO 2009/152542 A1 a generically configured injection device is known, with a distal end section and a proximal end section. The injection device can be automatically moved from a storage setting into an injection position. The device comprises a carrying housing configured as a sleeve, which is designed as subdivided into a front carrying housing part and a rear carrying housing part and comprises a distal end and a proximal end. The carrying housing is surrounded over most of its length by an activation sleeve, wherein the distal end of the carrying housing projects beyond the activation sleeve. In order to trigger the injection device, the activation sleeve can be moved in the axial direction relative to the carrying housing. Arranged in the carrying housing are a carpule and a needle arrangement. The carpule is in drive connection with a first drive module. By means of a securing device, the first drive module is held firmly in its position in relation to the carrying housing until its activation for the injection procedure. In addition, accommodated inside the carrying housing is a needle arrangement with a cannula, wherein, in the storage setting of the injection device, the needle arrangement is arranged in front of the carpule in the section of the distal end. Both ends of the cannula are also arranged inside the carrying housing. Also provided is a needle protection element, with a second activatable drive module in drive connection with it, the drive module moving the needle protection element from the non-effective position into the cover position. When viewed in the axial direction the first drive module is arranged behind the carpule, as a result of which more space is needed in the direction of the longitudinal extension.

SUMMARY OF THE INVENTION

The object of the present invention is to overcome the disadvantages of the prior art and to provide an injection device that allows for a multiple carpule arrangement, as well as allowing for a compact structural arrangement of the entire injection device.

This object is solved by an injection device in accordance with the claims. In particular the present invention provides an injector device according to claim 1.

The injection device according to the invention, in particular an autoinjector, serves to provide the simultaneous administration of at least two medications to a living being, in particular a person, which or who is in an emergency situation or exceptional situation. The injection device, configured here as an autoinjector, can be automatically moved from a storage setting into an injection position. The injection device, which has a distal end section that can be directed towards a patient and a proximal end section that faces away therefrom, comprises:

a. a carrying housing, said carrying housing being configured in a sleeve shape and comprising a distal end and a proximal end, b. an activation sleeve, said activation sleeve surrounding the carrying housing over a predominant part of its longitudinal extension, starting from the proximal end in the direction towards the distal end, wherein the distal end of the carrying housing projects beyond the activation sleeve, and the activation sleeve is moveable in an axial direction relative to the carrying housing, c. at least one carpule, with a piston arranged in it, said piston being movable in the axial direction, and with a medication received in the at least one carpule which is to be administered during the injection procedure, and wherein the at least one carpule is received in the carrying housing, d. a first drive module with a first drive means, said first drive module being in drive connection with the at least one carpule, and the first drive module being activatable by means of the activation sleeve, e. a securing device, said securing device holding the first drive module firmly in position relative to the carrying housing until the activation of the first drive module for the injection procedure, f. a needle arrangement with at least one cannula, said needle arrangement being arranged in front of the carpule in the section of the distal end when in the storage setting of the injection device, and in each case with both ends of the at least one cannula being arranged inside the carrying housing, g. a needle protection element, wherein when in the storage setting of the injection device, the needle position element is movable from a release position into a cover position, in which the needle end of the at least one cannula is covered, and wherein said needle end projects over the distal end of the carrying housing after the injection procedure, h. a second activatable drive module, with a second drive means, said second drive module arranged to move the needle protection element from a non-effective position into the cover position, i. and further comprises at least two carpules wherein, when viewed in cross-section, the at least two carpules are arranged next to one another in the carrying housing, j. wherein the first drive module further comprises a drive element, said drive element being arranged inside the carrying housing, k. wherein the drive element comprises in each case a number of piston rods that is equal to the number of carpules, said piston rods forming a composite structural unit, l. wherein at least one of the piston rods is configured in the form of a hollow cylinder that is closed at a first end region facing towards the distal end section, m. wherein the first drive means is arranged in the hollow cylinder of the at least one piston rod and/or n. wherein the first drive means is arranged in an accommodation part of the drive element, such that, when viewed in cross-section, it is arranged laterally next to the piston rods, and whereby the accommodation part forms a composite structural unit with the piston rods.

The advantage thereby achieved lies in the fact that, due to the provision of the drive element as a constituent part of the drive module, and due to the arrangement of multiple carpules next to one another, the drive means of the first drive module can be arranged directly inside one of the hollow cylinders of the piston rods and/or immediately next to them. Due to the possible arrangement of the drive means inside said piston rods, it is possible to achieve a shorter, more compact structure of the injection device.

If the first drive means is received next to the piston rods in its own accommodation part, then likewise a reduction in the structural length can also be achieved even with the arrangement of multiple carpules. By the formation of an individual drive element, at which the piston rods are provided, as well as, if appropriate, also an individual accommodation part laterally next to the piston rods, it is possible for a compact first drive module configuration to be achieved. In addition to this, however, it is also possible to provide a self-contained structural unit, outside which none of the first drive means are arranged. This allows for the necessarily sterilisation to be carried out more simply and more securely.

Advantageously an individual cannula can be arranged in front of each of the at least two carpules. This allows for recourse to be made to standard components. Additionally, however, this also make it possible for different cannula lengths to be selected for the medications being administered, whereby it is possible to control the penetration depth, and therefore the administration location, beneath the surface of the skin.

Another embodiment is characterised in that the drive element comprises a connection part that connects the piston rods and the accommodation part to one another at the end regions thereof that face towards the proximal end section, and wherein the piston rods and the accommodation part project in the distal direction from the connection part. Due to the provision of the additional connection part, it is possible for a compact structural unit to be formed. In addition to this, however, the opposing arrangement of the carpules in relation to one another is simplified, in particular if different carpule sizes are arranged next to one another.

A further possible embodiment has the features that the piston rods and the accommodation part are in each case configured in the form of hollow cylinders and are in each case configured as closed at the end regions thereof that face towards the distal end section. In this way material can be saved and, moreover, a completely closed outer surface can be formed, starting from the proximal end towards the distal end.

Advantageously, if only one of the pistons of a first carpule of the at least two carpules is connected to the piston rod allocated to the piston, and the other of the at least two carpules is held at the first carpule by means of a holding device. Due to the coupling of the piston rod to the piston, the two carpules can in this way be held at the drive element in a flexible manner in the event of loading being incurred due to a fall load event. In the storage setting, the drive element is also held in position relative to the carrying housing, as a result of which a specific location positioning of the carpules is possible.

Another possible and, if appropriate, alternative embodiment requires that each of the pistons is coupled to the piston rod allocated to it in each case, and the at least two carpules are held independently of one another at the drive element. This allows for each of the carpules to be held independently of one another at the common drive element at the piston rods arranged there. This allows for greater individual flexibility to be achieved with the holding of the carpules inside the carrying housing.

In a further embodiment the carrying housing comprises a front carrying housing part with a front accommodation space, and a rear carrying housing part with a rear accommodation space, and the two carrying housing parts can be connected to one another in a connection section in the axial direction, in two different longitudinal positions, in a first connection setting and in a second connection setting. Subdividing the carrying housing into the two carrying housing parts allows access into the interior, which is for the most part enclosed, so that sterilisation can be carried out, and, following the sterilisation, for the previously sterilised interior to be closed off entirely in relation to the outside surrounding environment. This allows all the components arranged inside the carrying housing to be kept sterile until the injection device is used.

Further preferably the two carrying housing parts can be connected to one another in the connection section by means of a coupling device. This allows for an additional guidance to be achieved between the housing parts which are to be coupled. In addition, however, this also provides a more reliable location positioning of the two carrying housings in relation to one another in at least one of the two connection settings, and in particular in both connection settings.

Additionally, or alternatively the rear carrying housing part comprises at least two guide extensions that project in the distal direction, said guide extensions being supported on the front carrying housing part and lying on it. Providing the additional guide extensions facilitates a better adjustment movement, free of tilting, between the two connection settings of the two carrying housing parts. In addition, however, it is also possible, in the first connection setting, for an access to be formed between the guide extensions into the accommodation space of the carrying housing.

Advantageously, in the first connection setting, the carrying housing parts exhibit a longitudinal extension which is greater than in the second connection setting. Accordingly, a perceptible relative location positioning to one another can be achieved between the two carrying housing parts. It is also thereby possible, however, for a gap to be formed between the two carrying housing parts in the larger longitudinal extension, so as to allow for the sterilisation of the accommodation space to be carried out.

Another alternative embodiment is characterised in that the front carrying housing part exhibits a longitudinal extension in the axial direction, which is selected in a value range with a lower limit of 60% and an upper limit of 95%, in particular with a lower limit of 70% and an upper limit of 85%, related to the total longitudinal extension of the two carrying housing parts in the second connection setting. Accordingly, the accommodation space serving for the sterilisation, inside the carrying housing, can be substantially extended in the direction towards the rear carrying housing part. In addition, however, due to the fact that a sealing element is provided in the connection region between the two carrying housing parts, the sealing of the accommodation space can be relocated onto the drive element. Since in the storage setting of the device the common drive element is held in position on the carrying housing, in particular on the rear carrying housing part, it is also possible, to avoid any relative changes of position between the sealing element and the common drive element occurring in the event of vibrating, and therefore avoid any contaminants, in particular germs, entering into the sterilised accommodation space.

A further possible and, if appropriate, alternative embodiment has the features that the distal end of the carrying housing, in particular the distal end of the front carrying housing part, comprises a number of openings that is equal to the number of cannulas, wherein said openings allow for the passage of the distal ends of the cannulas of the needle arrangement, and, in each case, are provided with a puncturable sealing plug, in a sealing position therein. This allows for an individual sealable passage region to be formed for each of the cannulas, which additionally allows for the accommodation space to be completely sealed.

A further embodiment makes provision for a sealing element to be provided, said sealing element being arranged between the front carrying housing part and the rear carrying housing part, and formed such as to run continuously over the circumference. The sealing element prevents an ingress of contaminants, in particular germs, into the sterilised accommodation space after the sterilisation the accommodation space.

Further preferably the sealing element comprises a sealing attachment at the distal end section that faces towards the front carrying housing part and runs over the entire circumference, wherein the first connection setting of the two carrying housing parts said sealing attachment is arranged at a distance from a face surface of the front carrying housing part; and, in the second connection setting of the two carrying housing parts, the sealing attachment is in sealing contact on the face surface of the front carrying housing part. Due to the provision of the sealing attachment, it is possible to create a simple sealing effect on the preferably flat-configured face surfaces between the two carrying housing parts.

A further preferred embodiment is characterised in that the sealing attachment of the sealing element is supported on a face surface of the rear carrying housing part, facing towards the front carrying housing part, and, further, that the sealing element extends into contact with the rear carrying housing part. This allows for a secure support of the sealing element to be achieved for the relative movement procedure between the two carrying housing parts. This also allows, however, in the second connection setting of the two carrying housing parts, for a secure location fixing of the sealing element to be achieved.

It can further be of advantage if the sealing element, in the storage setting of the device and with the carrying housing parts being in the second connection setting, is in full circumferential sealing contact with both the rear carrying housing part and the drive element arranged inside the housing part, in particular with the connection part of the element. This allows for an all-round continuous seal seat to be created in the region of the rear carrying housing part, between the drive element and the carrying housing, in particular the rear carrying housing part.

Another embodiment is characterised in that the carrying housing, in particular the rear carrying housing part, comprises at its distal end a transverse wall with a latch engagement cut-out opening arranged in it. Accordingly, a secure engagement position can be provided for the securing device, of which a part is arranged on the common drive element, as well as a relative positioning in relation to each other.

A further possible embodiment has the features that the securing device comprises at least one retention hook, said at least one retention hook being arranged on the drive element, in particular the connection part thereof, and wherein in the storage setting of the device, the at least one retention hook is held in the latch engagement cut-out opening in the transverse wall. This avoids the need for additional retention elements, and therefore for a compact configured drive element to be provided, which is arranged in the immediate proximity of the proximal end of the carrying housing in the storage setting of the device.

A further embodiment makes provision for the securing device to comprise a securing cap with a securing pin, arranged in the distal end section, and wherein by means of the securing pin, the at least one retention hook is held in an engaged position, in the storage setting of the device. Providing the securing cap with the securing pin, prevents any unintentional triggering of the device.

A further embodiment is characterised in that the proximal end region of the activation sleeve comprises a closure wall, and wherein said wall comprises a triggering means, in particular a triggering opening, aligned flush in relation to the engagement cut-out opening arranged in the transverse wall of the carrying housing, in particular of the rear carrying housing part. Due to the provision of the triggering means, it is possible, on actuation of the activation sleeve, for the automated release procedure to be initiated, once the securing device has been released.

A further preferred embodiment is characterised in that the second drive means of the second drive module is arranged outside the carrying housing, in particular outside the two carrying housing parts, but inside the activation sleeve. Accordingly, a protected arrangement of the second drive means can be achieved. In addition, this arrangement prevents tampering in a reliable manner.

Advantageously the second drive means of the second drive module extends in the axial direction between the needle protection element and the proximal end of the carrying housing, in particular of the rear carrying housing part. Due to the relatively long axial extension of the second drive means, it is possible in this way to achieve a slim configuration for this.

Advantageously the first drive means and/or the second drive means are respectively formed by a pressure spring, configured as a helical spring. This allows for recourse to be made to conventional commercial and economically priced components. This also allows for the movement force generated by the respective springs to be adjusted individually in a simple manner to meet the respective conditions of use.

Another alternative embodiment is characterised in that the second drive means is arranged on the side of the piston rods which, when viewed in cross-section, is opposite the accommodation part of the drive element. It is therefore likewise possible for a laterally offset arrangement of the second drive means to be created inside the injection device. This is additionally favoured in that the carrying housing is matched in its cross-section shape to the cylindrically configured carpules, and in this way a certain longitudinal guidance is already achieved on the outside of the carrying housing.

A further possible and, if appropriate, alternative embodiment requires that the longitudinal extension of the second drive means is guided at least in sections by means of guide elements, wherein the guide elements are arranged on an outer side of the carrying housing, in particular of the front carrying housing part. This allows for a folding outwards movement of the second drive means to be avoided, and for a tilting of these drive means between the carrying housing and the activation sleeve.

A further embodiment makes provision for the needle protection element to be held locked in its cover position in relation to the carrying housing in the proximal direction as well as in the axial direction. This makes it possible to prevent a piercing injury caused by the already used cannula ends of the cannulas, and therefore prevents the transfer of infections.

Another embodiment is characterised in that the simultaneous release takes place of both the first drive module as well as of the second drive module with the axial movement of the activation sleeve relative to the carrying housing. This therefore ensures both the administration of the medication as well as the subsequent protective positioning of the needle protection element occur automatically without contributory action by the person.

For a better understanding of the invention, this is explained in greater detail on the basis of the following figures.

Figure 2:
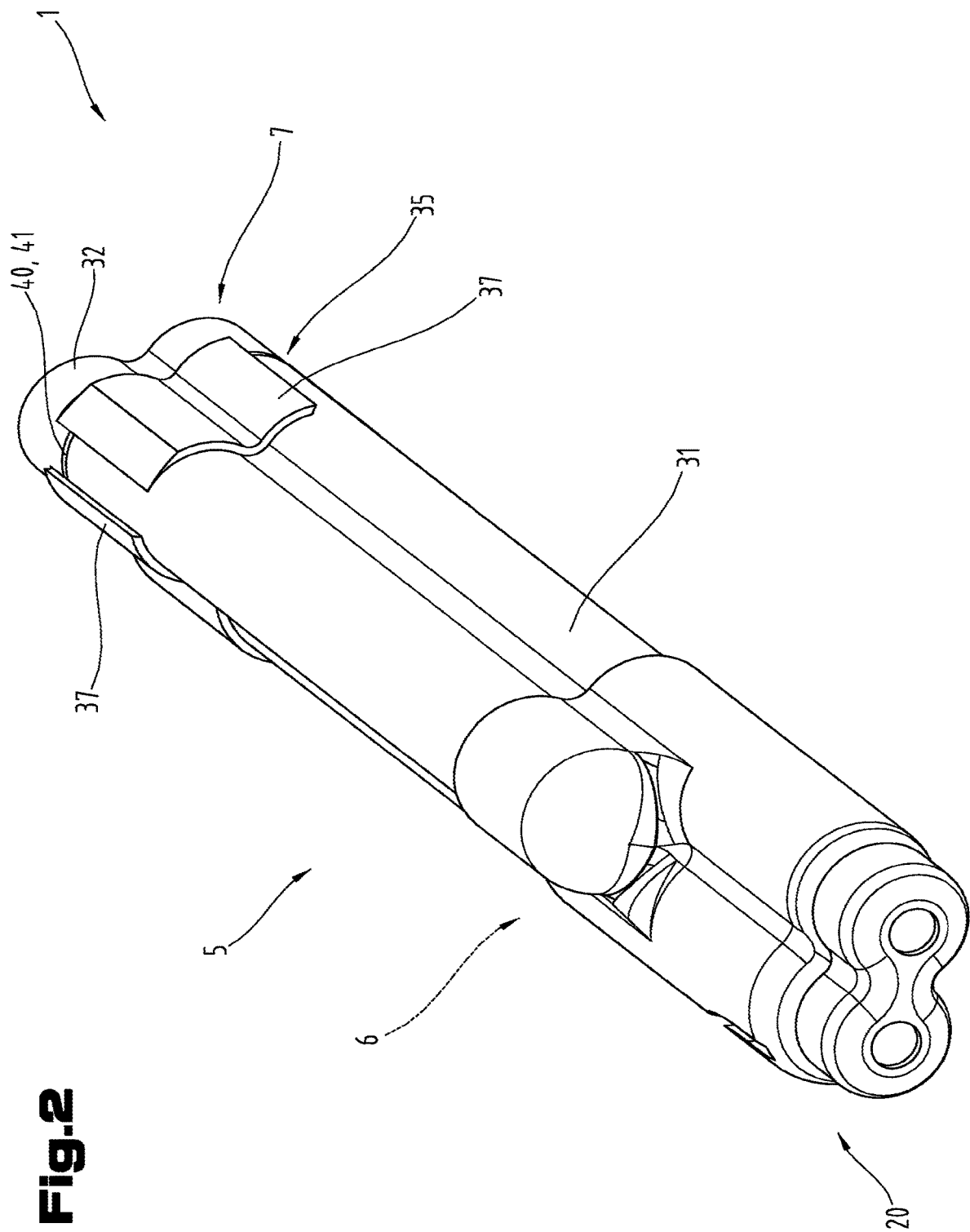
Figure 3:
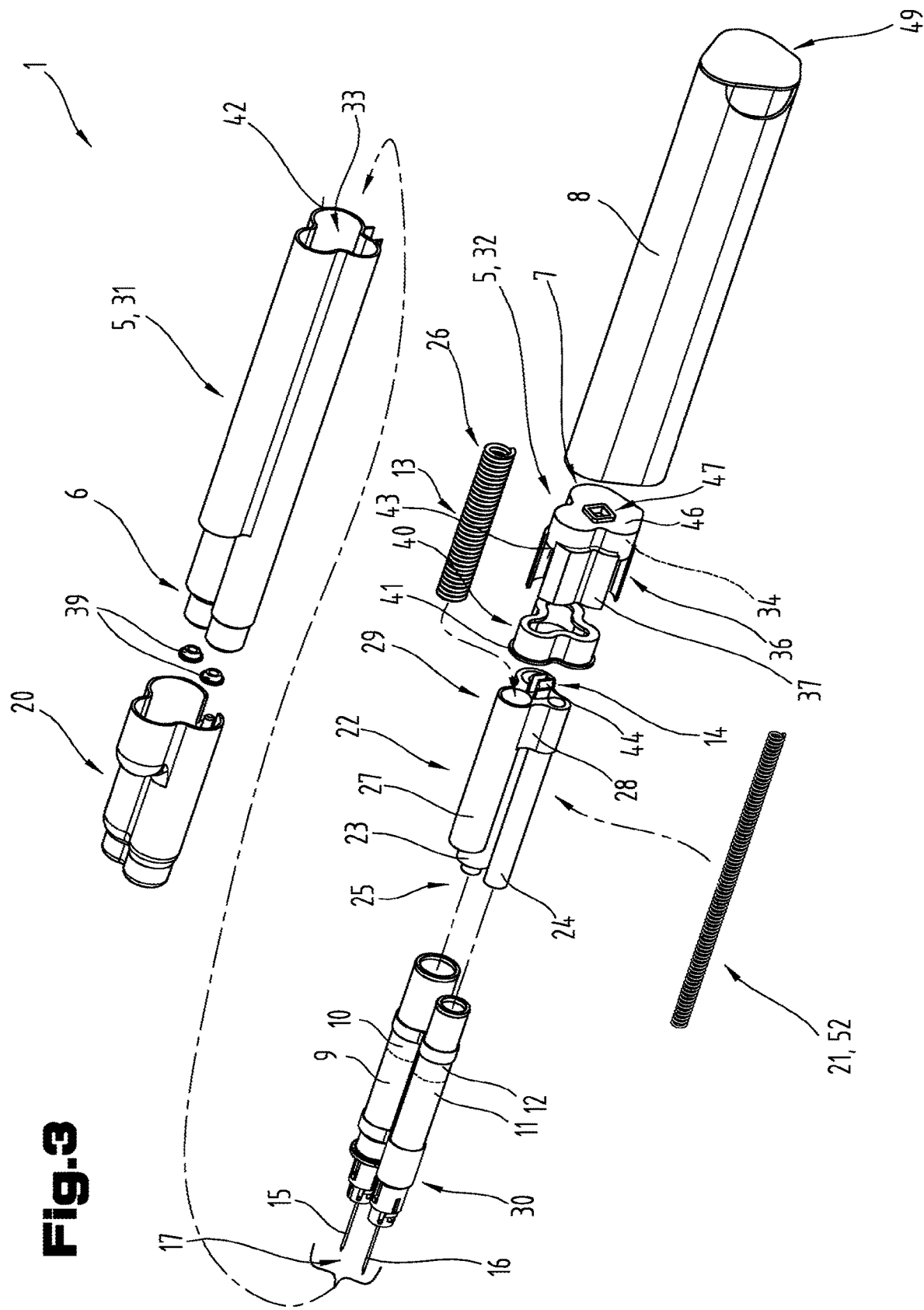
Figure 4:
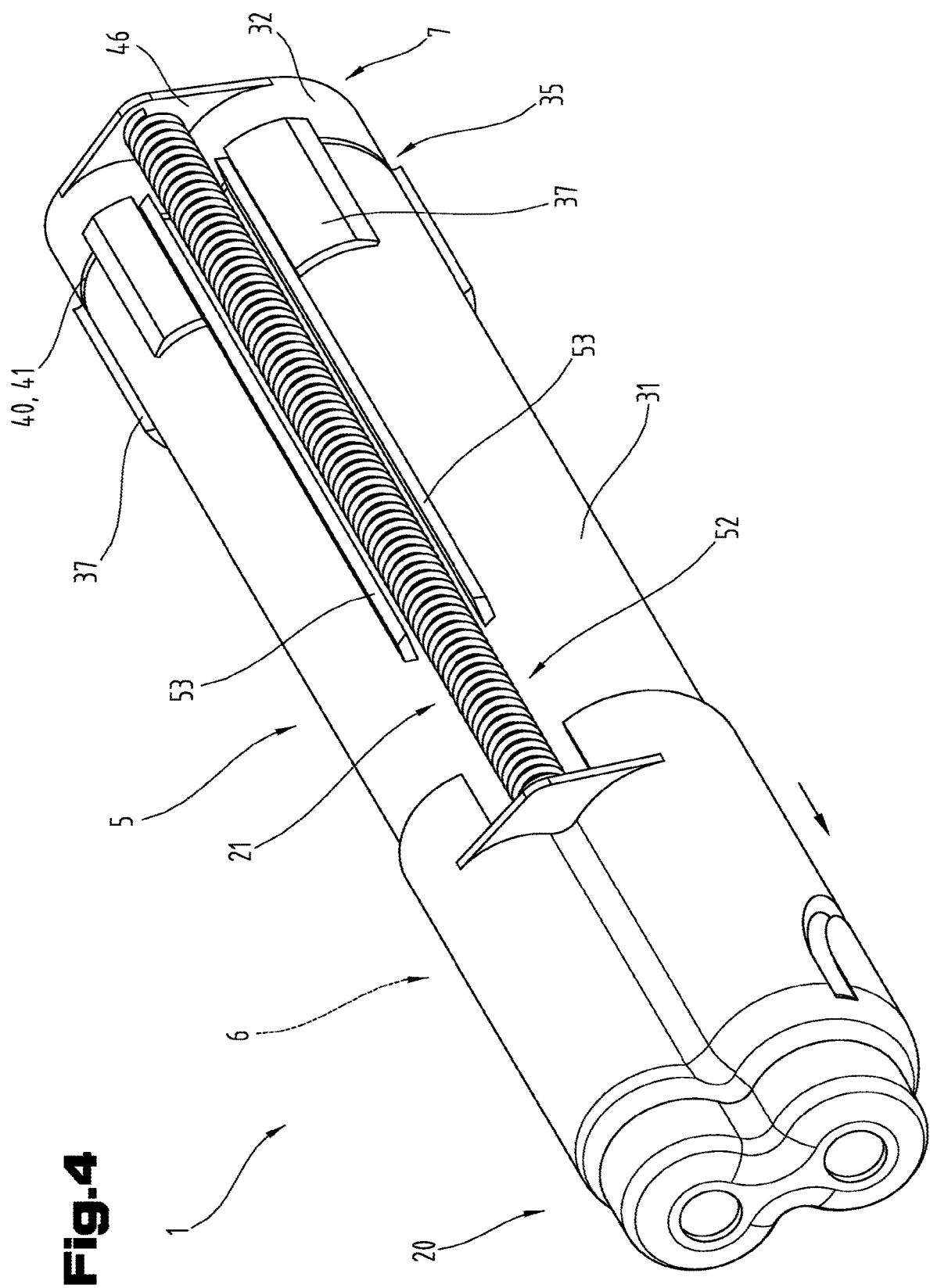

The figures show, in each case in a greatly simplified schematic representation:

FIG. 1 The injection device in an illustrative representation, in its secured storage setting;

FIG. 2 the injection device according to FIG. 1, in an illustrative representation but with the activation sleeve removed;

FIG. 3 the injection device according to FIGS. 1 and 2, in a separated arrangement of the component parts;

FIG. 4 the injection device according to FIG. 2, in an illustrative representation, in a view onto the second drive module for the needle protection element;

FIG. 5 the injection device according to FIG. 1, in its secured storage setting, in an axial section through the carpules;

FIG. 6 the injection device according to FIG. 5, after administration and with the needle protection element in the protective position;

FIG. 7 the injection device according to FIG. 5, in a cross-section according to the lines VII-VII in FIG. 5;

FIG. 8 the proximal end section of the injection device, in the sterilisation position in the axial section through the securing device.

By way of introduction, it may be pointed out that in the different embodiments described the same parts are provided with the same reference numbers or the same component designations, wherein the disclosures contained in the description as a whole can be transferred analogously to same parts with same reference numbers or same component designations. The location details selected in the description, such as upper, lower, lateral, etc. also relate to the figure being directly described and represented, and, in the event of a change of location, these location details are to be transferred analogously to the new location.

The term "in particular" is understood to mean hereinafter that this may relate to a possible more special configuration or more detailed specific description of an object or a method step but does not necessarily represent a mandatorily preferred embodiment or a mandatory form of procedure.

FIGS. 1 to 8 show different views and sections of an injection device 1, which can also be designated as an autoinjector. Such autoinjectors serve to administer at least one medication to a person 2 or a living creature, wherein the administration takes place automatically and therefore without contributory action by the operator. Such injection devices 1 are secured, in their storage setting, against unintentional triggering, wherein the triggering or actuation can only take place by deliberate release or disengagement of a securing device 14, described hereinafter. If release has been effected, triggering or actuation can follow, as a result of which the injection device 1 is automatically moved into an injection position, and, in this position, the medication or medications stored in the device are administered.

In some application situations it may be necessary for several medications to be held separately from one another in the injection device 1, without them coming in contact with one another before the administration. It is for such a purpose that the injection device 1 described hereinafter is provided. It is intended that at least two medications should be held ready so that the medicaments can then be administered to the patient 2 simultaneously in one administration procedure.

The injection device 1 comprises a distal end section 3, which in use is directed towards the patient 2, and a proximal end section 4, which faces away from the patient.

Described hereafter are individual modules or components of the injection device 1, which the device can comprise. In addition, for the location indication, the designations front and rear are used, and in this context 'front' is assigned to the patient facing or distal end section 3 and 'rear' to the proximal end section 4.

The injection device 1 therefore comprises a carrying housing 5, which is configured in the form of a sleeve and comprises a distal end 6 and a proximal end 7. Also provided is an activation sleeve 8, which surrounds the carrying housing 5 over a predominant part of its longitudinal extension, starting from the proximal end 7 in the direction towards the distal end 6. In this arrangement, the distal end 6 of the carrying housing 5 projects beyond the activation sleeve 8 in the distal direction. The activation sleeve 8 is movable relative to the carrying housing 5 in the axial direction and guided on it. As will be described hereinafter, this relative movement serves for the release and therefore the associated administration of the medication or the medications.

In the present exemplary embodiment, two carpules 9, 11 are arranged in the carrying housing 5, accommodating the medications which are to be administered in each case but are not designated in greater detail. In a known manner, arranged inside each of the carpules 9, 11 is a piston 10, 12, for providing a sealing closure of the carpules 9, 11 in their proximal end regions. For the administration of the medications, the carpules 9, 11 are in drive connection with a first drive module 13. The at least two carpules 9, 11, seen in cross-section, are arranged next to one another in the carrying housing 5. The activation or triggering of the drive module 13 can take place by means of the activation sleeve 8, after release of the securing device 14.

The securing device 14 holds at least the first drive module 13 securely in its position in relation to the carrying housing 5 until its activation for the injection procedure.

It can also be of advantage if, for each of the carpules 9, 11, in each case an individual cannula 15, 16 is provided. The cannulas 15, 16 form a needle arrangement 17. In the storage setting of the injection device 1, the needle arrangement, and in particular its cannulas 15, 16, are arranged in front of the respective carpules 9, 11, in the section of the distal end 7. Each of the cannulas 15, 16 comprises in turn cannula ends 18, 19, wherein, in the storage setting, both of the cannula ends 18, 19 respectively are also arranged inside the carrying housing 5. In the storage setting, likewise, the proximal ends 19 of the cannulas 15, 16, are arranged in front of the respective carpules 9, 11. The puncture, and therefore the access to the medication, does not take place until the activation of the injection device 1 by the activation sleeve 8.

In order to cover the distal ends 18 of the cannulas, which project beyond the carrying housing 5 after the administration of the medications, provision can also be made for a needle protection element 20. If the injection device 1 is in the storage setting, the needle protection element 20 is arranged in what is referred to as a release position for the distal ends 18, in which unhindered movement of the cannulas 15, 16 and the subsequent administration can take place. If the administration procedure has begun, and the distal cannula ends 18 are still in the inserted injection position in the patient 2, the needle protection element 20 can be located in a position on the skin or on an item of clothing if the patient 2 is a person. For the automated adjustment movement of the needle protection element 20, a second triggerable or activatable drive module 18 can be provided, which is in drive connection with the needle protection element 20. This therefore makes it possible for the needle protection element 20 to move beyond the distal cannula ends 18 after the injection procedure, projecting from the carrying housing 5 over the distal end 7, into a cover position protecting these ends.

The drive module 13 can further comprise a drive element 22, which is likewise arranged inside the carrying housing 5. The drive element 22 comprises in each case a number of piston rods 23, 24 which is equal to the number of carpules 9, 11. The piston rods 23, 24 form a composite structural unit.

It is also possible for at least one of the piston rods 23, 24 to be configured in the form of a hollow cylinder and is formed as closed at an end region 25 that faces towards the distal end section 3. In this case, it would be possible, depending on the clear internal dimension of the piston rod 23, 24, for a first drive means 46 of the first drive module 13 to be arranged or accommodated in the at least one piston rod 23, 24 configured in the form of a hollow cylinder.

In addition to or independently of this, however, it would also be possible to provide an individual accommodation part 27 on the drive element 22, which, when seen in cross-section, is arranged laterally next to the piston rods 23, 24. The first drive means 26 to be arranged or accommodated inside this. It would also be possible, however, for a multiple arrangement of first drive means 26 to be provided, with which in each case a first drive means 26 is located both inside at least one of the piston rods 23, 24 as well as inside the accommodation part 27.

If the accommodation part 27 is provided, this forms a composite structural unit with the piston rods 23, 24. The drive element 22 can further comprise a connection part 28, by means of which the at least two piston rods 23, 24, and, if provided, also the accommodation part 27, are connected to one another to form a structural unit. Each of the piston rods 23, 24, and, if provided, also the accommodation part 27, exhibit respective end regions 29, wherein the mutual connection to form a structural unit takes place in the area of said end regions 29. Starting from the common connection part 28, the at least two piston rods 23, 24 and, as appropriate, the accommodation part 27 project from this in the distal direction (i.e., towards the 'front' of the device).

In order to save material and weight, it may be advantageous if the at least two piston rods 23, 24 and the accommodation part 27 of the drive element 22 are respectively configured in the form of hollow cylinders, and in each case are formed as closed in at first end regions 25 thereof which face towards the distal end section 3.

There are various different possibilities for holding the carpules 9, 11, on the drive element 22. The first possibility makes provision for only one of the pistons 10, 12 of a first of the at least two carpules 9, 11 to be coupled to the piston rod 23, 24 allocated to the piston 10, 12, and therefore to be brought into drive connection. The other of the at least two carpules 11, 9 is held by means of a holding device 30 at the first of the at least two carpules 9, 11. The other piston rod 24, 23, which is not coupled, serves only to drive forward the carpule 11 and the piston 12 arranged within it.

In an alternative arrangement, provision is made for each of the pistons 10, 12 to be coupled to the piston rods 23, 24 allocated respectively to the pistons, and the at least two carpules 9, 11 are held on the drive element 22 independently of one another.

In order to facilitate the assembly and the sterilisation of components arranged inside the carrying housing 5, the carrying housing 5 is subdivided into a first carrying housing part 31 and a rear carrying housing part 32. The front carrying housing part 31 delimits a front accommodation space 33 and the rear carrying housing part 32 delimits a rear accommodation space 34. To provide mutual connection, the two carrying housing parts 31, 32 are connected to one another in a connection section 35 in the axial direction, in two different longitudinal positions, in a first connection setting and a second connection setting. This can be done by means of a coupling device 36, not represented in any greater detail. Accordingly, the carrying housing parts 31, 32 in the first connection setting exhibit a greater longitudinal extension in relation to the second connection setting.

In the present exemplary embodiment, the front carrying house part 31 exhibits a longitudinal extension in the axial direction, which is selected in a value range with a value with a lower limit of 60% and a value with an upper limit of 95% related to the overall longitudinal extension of the two carrying housing parts 31, 32, in their second connection setting. It has, however, also transpired that a value range is favourable with which a value is selected with a lower limit of 70% and a value with an upper limit of 85% related to the overall longitudinal extension of the two carrying housing parts 31, 32, in their second connection setting.

It is further represented that the rear carrying housing part 32 can comprise at least two guide extensions 37 projecting in the distal direction. It would also be possible, however, for the guide extensions 37 to be provided either only on the front carrying housing part 31 or also on reciprocal sides. The guide extensions 37 are supported at the front carrying housing part 31 and/or at the rear carrying housing part 32, lying in contact with them.

In order to avoid an undesirable ingress of dirt contamination to the cannulas 15, 16 and to the carpules 9, 11 during the storage setting of the device, provision is further made for the distal end 7 of the carrying housing 5, in particular the distal end 7 of the front carrying housing part 31, to exhibit a number of openings 38, equal to the number of cannulas 15, 16. Since preferably the number of cannulas 15, 16 is selected as equal to the number of carpules 9, 11, this number also corresponds to the number of openings 38. Arranged in each case in the individual openings 38 is a puncturable sealing plug 39, in a sealing position, wherein, by the openings 38, the through passage of the distal cannula ends 18 of the cannulas 15, 16 is made possible. During the administration procedure, the sealing plugs 39 are also punctured by the cannulas 15, 16.

In order to provide mutual sealing between the two mutually facing ends of the two carrying housing parts 31, 32, a sealing element 40 is also provided, which is formed such as to run continuously over the circumference. The sealing element 40 comprises at its distal end section, facing towards the front carrying housing part 31, a sealing attachment 41, running continuously over the entire circumference. The preferably flange-shaped sealing attachment 41 can further be configured such that it projects between mutually facing face surfaces 42, 43 of the two carrying housing parts 31, 32; see FIG. 8. In the first connection setting, described hereinbefore, a circumferential gap is also formed between the mutually facing face surfaces of the two carrying housing parts 31, 32, into which gap the sealing attachment 41 can also project. In order to provide at least one access for carrying out the sterilisation by means of a gasification process into the front accommodation space 33 of the front carrying housing part 31, the gap width is to be selected as sufficiently large for the gap not to be completely closed by the sealing attachment 41 located in it.

With this exemplary embodiment, provision is made for the sealing attachment 41, in the first connection setting of the two carrying housing parts 31, 32, to be arranged at a distance from the face surface 42 of the front carrying housing part 31. In the second connection setting of the two carrying housing parts 31, 32, the sealing attachment 41 is in sealing contact on the face surface 42 of the front carrying housing part 31. The sealing attachment 41 of the sealing element 40 can also be supported on the face surface 43 of the rear carrying housing part 32, facing the front carrying housing part 31. The circumferential sealing element 40 can also extend into the rear carrying housing part 32 and be supported lying in contact on its inner surface.

It is also important that the sealing element 40, in the storage setting of the device, and with the carrying housing parts 31, 32 being in the second connection setting, is also in sealing contact over the full circumference on the drive element 22, arranged in the interior of the housing parts. A circumferential support of the sealing element 40 is preferably also to be provided on the inner surface of the rear carrying housing part 32. In any event, at least the front accommodation space 33, in the storage setting of the device, is to be completely sealed against the outside surrounding environment by means of the sealing element 40. The sealing contact of the sealing element 40 is to be applied in particular at the outer circumference of the connection part 28 of the drive element.

The securing device 14 comprises at least one retention hook 44, and preferably a plurality thereof, which is or are arranged with at least one retention hook 44 on the drive element 22. The connection part 28 of the drive element 22 comprises in this context a face wall, aligned preferably in the perpendicular direction in relation to a longitudinal axis 45 of the injection device 1, from which wall the at least one retention hook 44 is arranged projecting in the proximal direction. For the latch engagement of the at least one retention hook 44, the carrying housing 5, in particular the rear carrying housing part 32, can comprise at its distal end a transverse wall 46, with a latch engagement cut-out opening 47 arranged in it. Accordingly, the at least one retention hook 44, in the secure setting as well as in the storage setting, can be held in the latch engagement cut-out opening 47 of the transverse wall 46. In this setting, the at least one retention hook 44 engages behind the transverse wall 46, on its side facing the proximal end section 4. The first drive means 26 is supported on the one hand at the rear carrying housing part 32, and in the accommodation part 27, imposing preliminary tension on it. If the securing device 14 is released, the drive element 22 is displaced in the direction towards the distal end 6 or the distal end section 3.

The securing device 14 can further comprise a securing cap 48, with a securing pin 49, arranged in the proximal end section 4 of the injection device 1. By means of this securing pin 49, the at least one retention hook 44, in the storage setting, is held in a latched setting at the carrying housing 5. In order to release or free the at least one retention hook 44, it is first to be freed by the securing pin 49.

The triggering, and, associated with this, the freeing of the at least one retention hook 44, is carried out by means of the activation sleeve 8. For this purpose, the sleeve comprises in its proximal end region a closure wall 50. Provided at the closure wall 50 is a triggering means 51, which, in this exemplary embodiment, is configured as a trigger opening. The triggering means 51 is aligned in the axial direction flush in relation to the latch engagement cut-out opening 47 arranged in the transverse wall 46 of the carrying housing 5, in particular of the rear carrying housing part 32.

The needle protection element 20 is in drive connection with the second drive module 21; see FIG. 4. The second drive module 21 comprises at least one second drive means 52, which is arranged outside the carrying housing 5, in particular the two carrying housing parts 31, 32, and inside the activation sleeve 8. The second drive means 52 extends in the axial direction between the needle protection element 20 and the proximal end of the carrying housing 5, in particular the rear carrying housing part 32. So, for example, the face wall of the connection part 28 can form a stop for the second drive means 52.

It is advantageous if the first drive means 26 and the second drive means 52 are in each case formed by a pressure spring configured as a helical spring. This allows for recourse to be made to standard components. It therefore becomes possible to select a slim configuration of the second drive means 52. Accordingly, the second drive means 52, configured as a helical spring, can be arranged on the side of the piston rods 23, in cross-section located opposite the accommodation part 27 of the drive element 22, between the carrying housing 5 and the activation sleeve 8.

In order to avoid the folding outwards movement of the second drive means 52, configured as a helical spring, the drive means can be guided in its longitudinal extension at least in part by means of guide elements 53. The guide elements 53 can be arranged on an outer side of the carrying housing 5, in particular of the front carrying housing part 31, and can be formed by webs or ribs.

In order to prevent a piercing injury caused by the already used cannulas 15, 16, the needle protection element 20 can be held locked in its cover setting in the proximal direction as well as in the axial direction relative in relation to the carrying housing 5 by means of a locking device, not represented in greater detail.

The axial adjustment movement carried out by the activation sleeve 8 in relation to the carrying housing 5 has the effect of the simultaneous release of both the first drive module 12 as well as of the second drive module 21.

In conclusion, it may also be pointed out that the configuration of the injection device 1 described hereinbefore, in particular of the autoinjector, in a number of component groups, corresponds to that configuration such as in WO 2009/152542 A1, by a forerunner company of the present Applicants. Accordingly, for the configuration of the needle arrangement 17, and for the guiding and locking engagement of the needle protection element 20 and of the carpules 9, 11, reference is made to the disclosure contained in the WO-A1.

The exemplary embodiments show possible configuration variants, wherein it may be noted at this juncture that the invention is not restricted to the configuration variants which are specially represented, but rather that diverse combinations of the individual embodiment variants among one another are possible, and that this variation possibility, on the basis of the teaching with regard to technical action by way of the present invention, lies within the ability of the person skilled in the art engaged in this sector.

The range of protection is determined by the claims. The description and the drawings, however, are to be drawn on for the interpretation of the claims. Individual features or feature combinations from the different exemplary embodiments shown and described can represent independent inventive solutions. The object underlying the independent inventive solutions can be derived from the description.

All details relating to value ranges in the present description are to be understood such that they encompass any and all part ranges; for example, the indication 1 to 10 is to be understood such that all part ranges, from the lower limit 1 to the upper limit 10, are encompassed, i.e. all part ranges beginning with a lower limit of 1 or greater and ending at an upper limit of 10 or less, e.g. 1 to 1.7, or 3.2 to 8.1, or 5.5 to 10.

For the sake of good order, it may be mentioned in conclusion that for better understanding of the structure, elements have in part been represented not to scale, and/or enlarged or reduced in size.

Reference number list

1 Injection device
2 Patient
3 Distal end section
4 Proximal end section
5 Carrying housing
6 Distal end
7 Proximal end
8 Activation sleeve
9 Carpule
10 Piston
11 Carpule
12 Piston
13 First drive module
14 Securing device
15 Cannula
16 Cannula
17 Needle arrangement
18 First cannula end
19 Second cannula end
20 Needle protection element
21 Second drive module
22 Drive element
23 Piston rod
24 Piston rod
25 First end region
26 First drive means
27 Accommodation part
28 Connection part
29 Second end region
30 Retaining device
31 Front carrying housing part
32 Rear carrying housing part
33 Front accommodation space
34 Rear accommodation space
35 Connection section
36 Coupling device
37 Guide extension
38 Opening
39 Sealing plug
40 Sealing element
41 Sealing attachment
42 Face surface
43 Face surface
44 Retention hook
45 Longitudinal axis
46 Transverse wall
47 Latch engagement cut-out
48 Securing cap
49 Securing pin
50 Closure wall
51 Triggering means
52 Second drive means
53 Guide element

What is claimed is:

1. An autoinjector comprising:
a distal end section configured to be directed towards a patient;
a proximal end section configured to face away from the patient;
a carrying housing comprising a distal end and a proximal end;
an activation sleeve surrounding a predominant part of a longitudinal extension of the carrying housing and extending from the proximal end in a direction towards the distal end, such that the distal end of the carrying housing projects beyond the activation sleeve, the activation sleeve being moveable in relation to the carrying housing in an axial direction;
a first carpule positioned in the carrying housing, the first carpule including a first piston that is adjustable in the axial direction and a medication for administration during an injection procedure;
a second carpule positioned in the carrying housing, the second carpule including a second piston that is adjustable in the axial direction and a medication for administration during an injection procedure, and when viewed in cross-section, the first carpule and second carpule are arranged next to one another in the carrying housing;
a first drive module with a first drive means, the first drive module being in drive connection with at least one of the first carpule and second carpule, and being activatable by the activation sleeve;
a securing device to secure the first drive module in position relative to the carrying housing until activation of the first drive module for the injection procedure; and
a needle arrangement with at least one cannula, the needle arrangement being positioned in front of at least one of the first carpule and second carpule in the distal end section such that the at least one cannula is arranged inside the carrying housing,
wherein the first drive module further comprises a drive element arranged inside the carrying housing, the drive element including a first piston rod and a second piston rod that form a composite structural unit,
wherein at least one of the first piston rod and second piston rod is a hollow cylinder that is closed at a first end section that faces towards the distal end section, and
wherein the first drive means is arranged in the hollow cylinder of the at least one of the first piston rod and second piston rod.

2. The autoinjector according to claim 1, wherein the at least one cannula includes a first cannula arranged in front of the first carpule and a second cannula arranged in front of the second carpule.

3. The autoinjector according to claim 1, wherein the first piston of the first carpule is coupled to the first piston rod, and wherein the second carpule is held by a holding device to the first carpule.

4. The autoinjector according to claim 1, wherein each of the first piston and the second piston is coupled to the first piston rod or the second piston rod, respectively, and the first carpule and the second carpule are held independently from one another on the drive element.

5. The autoinjector according to claim 1, wherein the carrying housing comprises a front carrying housing part with a front accommodation space and a rear carrying housing part with a rear accommodation space, and the front and rear carrying housing parts are configured to be connected to one another in a connection section in the axial direction in two different longitudinal positions in a first connection setting and a second connection setting.

6. The autoinjector according to claim 5, wherein the front and rear carrying housing parts are configured to be connected to one another in the connection section by a coupling device.

7. The autoinjector according to claim 5, wherein the rear carrying housing part comprises at least two guide extensions that project in a distal direction, the at least two guide extensions being supported by lying in contact on the front carrying housing part.

8. The autoinjector according to claim 5, wherein in the first connection setting the front and rear carrying housing parts exhibit a greater longitudinal extension in relation to the second connection setting.

9. The autoinjector according to claim 5, wherein the front carrying housing part exhibits a longitudinal extension in the axial direction, which is selected in a value range with a lower limit of 60% and an upper limit of 95%, or with a lower limit of 70% and an upper limit of 85%, related to a total longitudinal extension of the front and rear carrying housing parts in the second connection setting.

10. The autoinjector according to claim 5, wherein a distal end of the front carrying housing part comprises a number of openings that is equal to a number of cannulas, wherein the openings allow for through passage of distal ends of the cannulas, and in each case a puncturable sealing plug is arranged in each of the openings in a sealing position.

11. The autoinjector according to claim 5, further comprising a sealing element arranged between the front carrying housing part and the rear carrying housing part.

12. The autoinjector according to claim 11, wherein the sealing element comprises, at the distal end section that faces towards the front carrying housing part, a sealing attachment, wherein in the first connection setting of the front and rear carrying housing parts the sealing attachment is arranged at a distance from a face surface of the front carrying housing part, and in the second connection setting of the front and rear carrying housing parts the sealing attachment is in sealing contact at the face surface of the front carrying housing part.

13. The autoinjector according to claim 12, wherein the sealing attachment of the sealing element is supported on a face surface of the rear carrying housing part, facing towards the front carrying housing part, and wherein the sealing element extends into contact with the rear carrying housing part.

14. The autoinjector according to claim 11, wherein the sealing element, in a storage setting of the autoinjector and with the front and rear carrying housing parts being in the second connection setting, is in sealing contact over a full circumference of both the rear carrying housing part and a connection part of the drive element that is arranged inside the front and rear carrying housing parts.

15. The autoinjector according to claim 5, wherein the rear carrying housing part comprises at a distal end thereof a transverse wall having a latch engagement cut-out opening therein.

16. The autoinjector according to claim 15, wherein the securing device comprises at least one retention hook, the at least one retention hook being arranged on a connection part of the drive element and wherein, in a storage setting of the autoinjector, the at least one retention hook is held in the latch engagement cut-out opening of the transverse wall.

17. The autoinjector according to claim 16, wherein the securing device comprises a securing cap with a securing pin, arranged in the distal end section, and wherein the securing pin is configured to hold the at least one retention hook in a latch engaged setting when the autoinjector is in the storage setting.

18. The autoinjector according to claim 15, wherein a proximal end region of the activation sleeve comprises a closure wall upon which a triggering opening of a triggering means is arranged, wherein the triggering means is aligned in the axial direction flush in relation to the latch engagement cut-out opening arranged in the transverse wall of the rear carrying housing part.

* * * * *